US012651642B2

(12) United States Patent
    Odaibo

(10) Patent No.: US 12,651,642 B2
(45) Date of Patent: Jun. 9, 2026

(54) EARLY FUSION OF NATURAL AND PROTEIN LANGUAGE MODELS FOR GENERATIVE AI-BASED PROTEIN AND DRUG DESIGN

(71) Applicant: Stephen Gbejule Odaibo, Sugar Land, TX (US)

(72) Inventor: Stephen Gbejule Odaibo, Sugar Land, TX (US)

(73) Assignee: Deep EigenMatics, Inc., Sugar Land, TX (US)

( * ) Notice: Subject to any disclaimer, the term of this patent is extended or adjusted under 35 U.S.C. 154(b) by 0 days.

(21) Appl. No.: 19/193,962

(22) Filed: Apr. 29, 2025

(65) Prior Publication Data

US 2025/0279161 A1     Sep. 4, 2025

(51) Int. Cl.
    *G16B 15/30*     (2019.01)
    *G06N 3/04*      (2023.01)
    *G16B 40/20*     (2019.01)
(52) U.S. Cl.
    CPC .............. *G16B 15/30* (2019.02); *G06N 3/04* (2013.01); *G16B 40/20* (2019.02)
(58) Field of Classification Search
    None
    See application file for complete search history.

(56) References Cited

FOREIGN PATENT DOCUMENTS

CN        117912545 A   *  4/2024   ............... G06N 3/08

OTHER PUBLICATIONS

Wei, Jason, et al. "Chain-of-thought prompting elicits reasoning in large language models." Advances in neural information processing systems 35 (2022): 24824-24837.*
English machine translation of Zhou CN-117912545-A. (Year: 2025).*
Gao, Wenhao, and Connor W. Coley. "The synthesizability of molecules proposed by generative models." Journal of chemical information and modeling 60.12 (2020): 5714-5723.*
Merrifield, Robert B. "Solid phase peptide synthesis. I. The synthesis of a tetrapeptide." Journal of the American Chemical Society 85.14 (1963): 2149-2154.*

* cited by examiner

*Primary Examiner* — G. Steven Vanni

(57)              ABSTRACT
Methods and apparatus using a mixture of representation modalities including natural language, protein sequence, protein structure, property-vector, and small molecule drug representations to jointly train a neural network which accepts mixed modality queries as input and produces mixed modality output responses including representations of proteins for synthesis and of small molecule drugs for manufacture. In one embodiment of the invention, multicapitate transformers wherein each decoder head has a distinct loss function and represents a distinct modality, are used. Modality-specific embeddings are implemented for the mixed modality input query, and an autoregressive process yields the output protein for synthesis or small molecule drug for manufacture.

20 Claims, 11 Drawing Sheets

Specification includes a Sequence Listing.

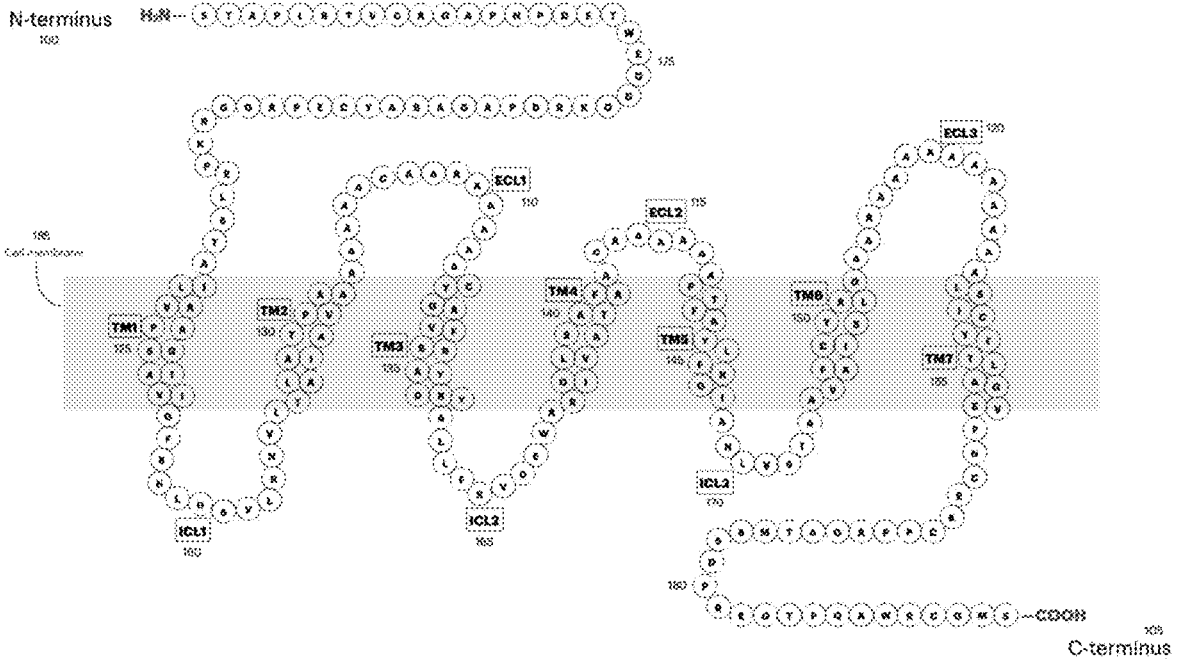
FIG. 1 A 2D representation of a G-Protein Coupled Receptor (GPCR).

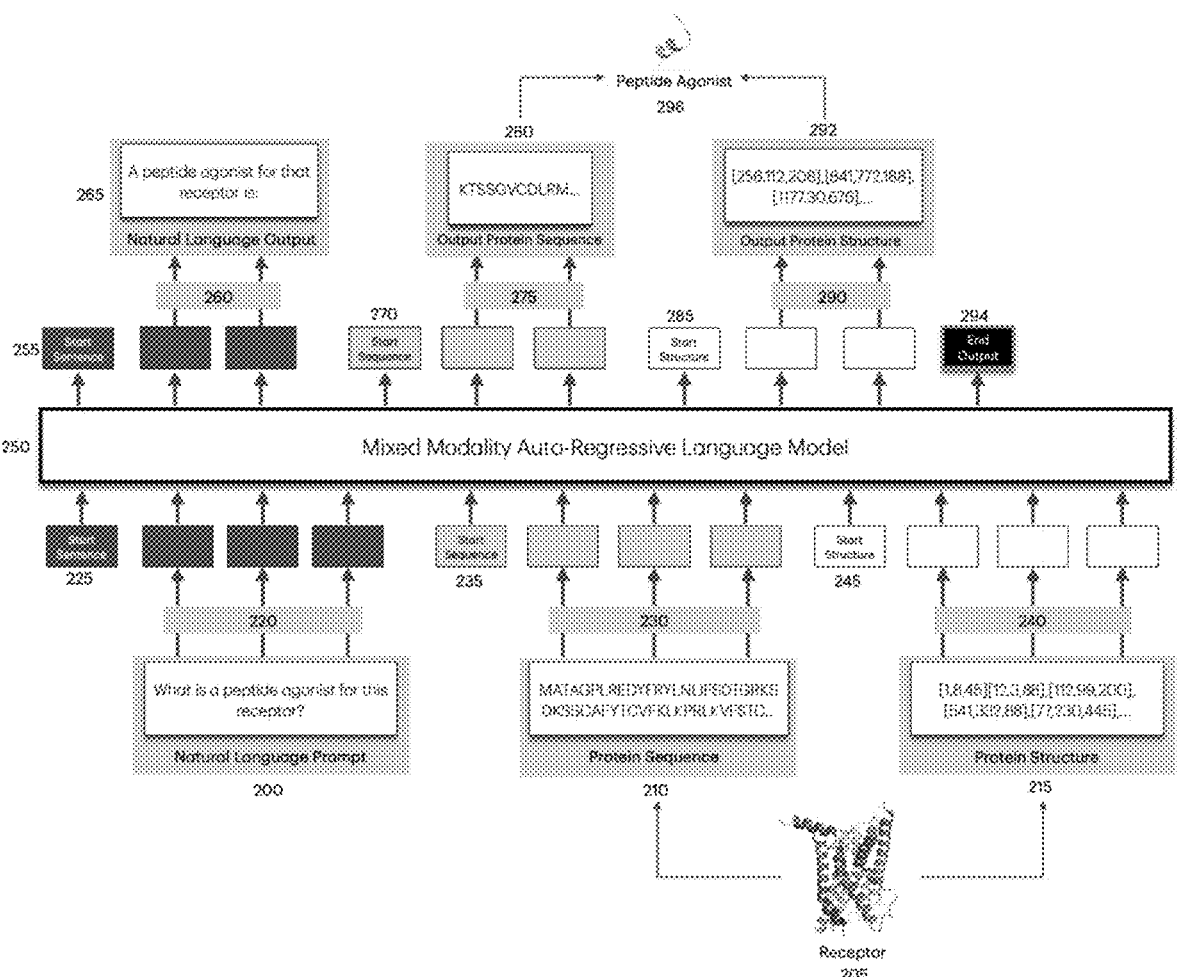
FIG. 2 Illustrative Overview of Inference Process with a Mixed-Modal Early-Fusion
Language Model for Protein and Drug Design.

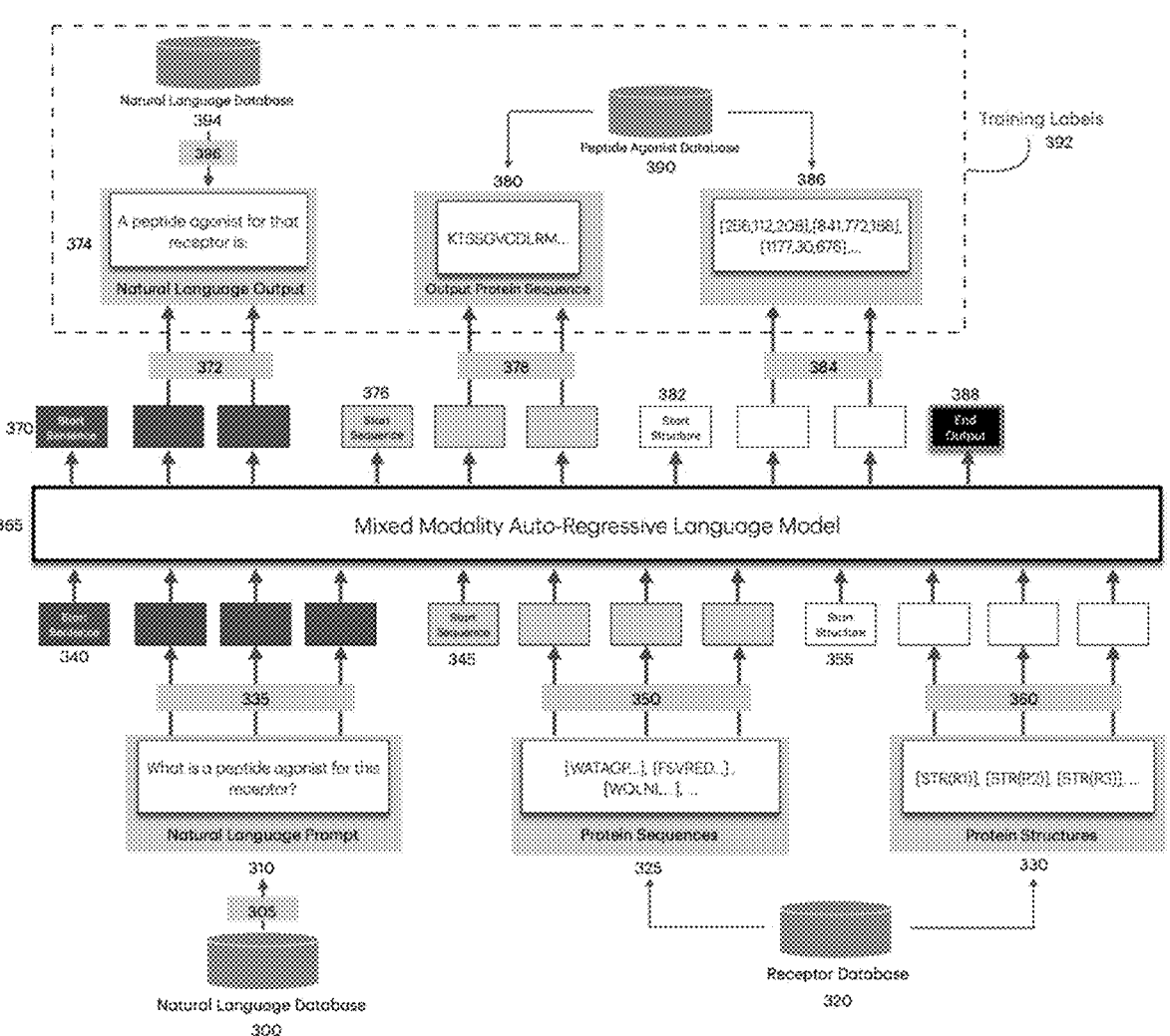
FIG. 3 Illustrative Overview of a Training Process for a Mixed-Modal Early-Fusion
Language Model for Protein Drug Design.

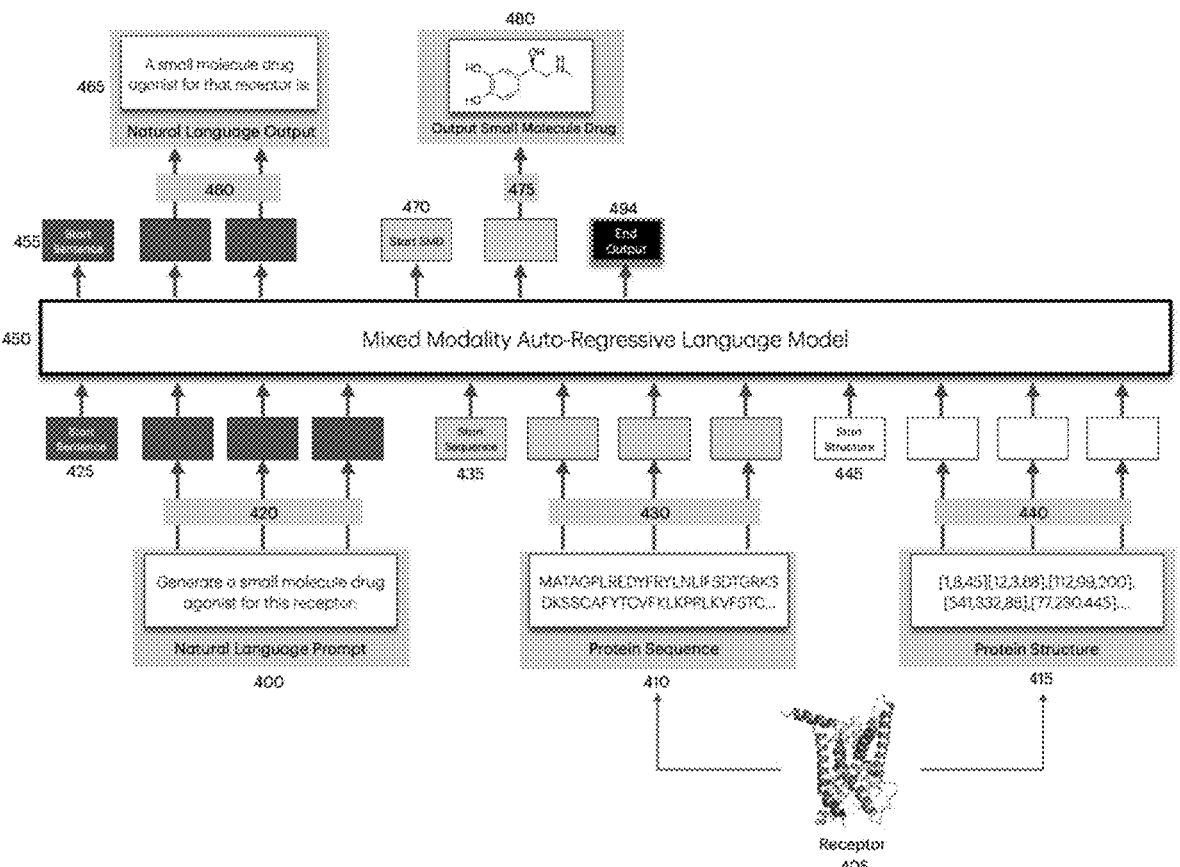
FIG. 4 Illustrative Overview of the Inference Process with a Mixed-Modal Early-Fusion
Language Model for Small Molecule Drug Design.

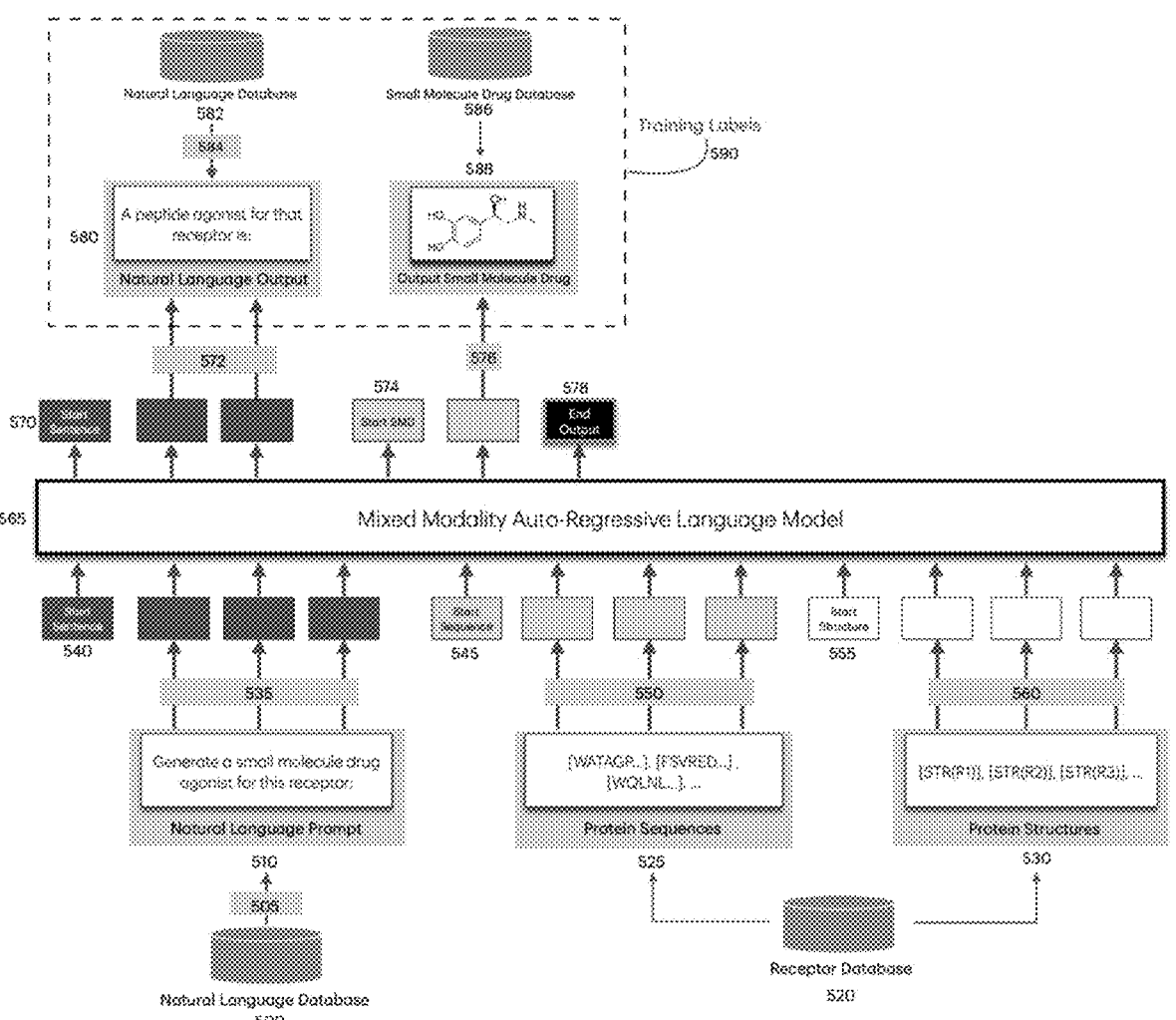
FIG. 5 Illustrative Overview of the Pre-Training Process for a Mixed-Modal Early-Fusion
Language Model for Small Molecule Drug Design.

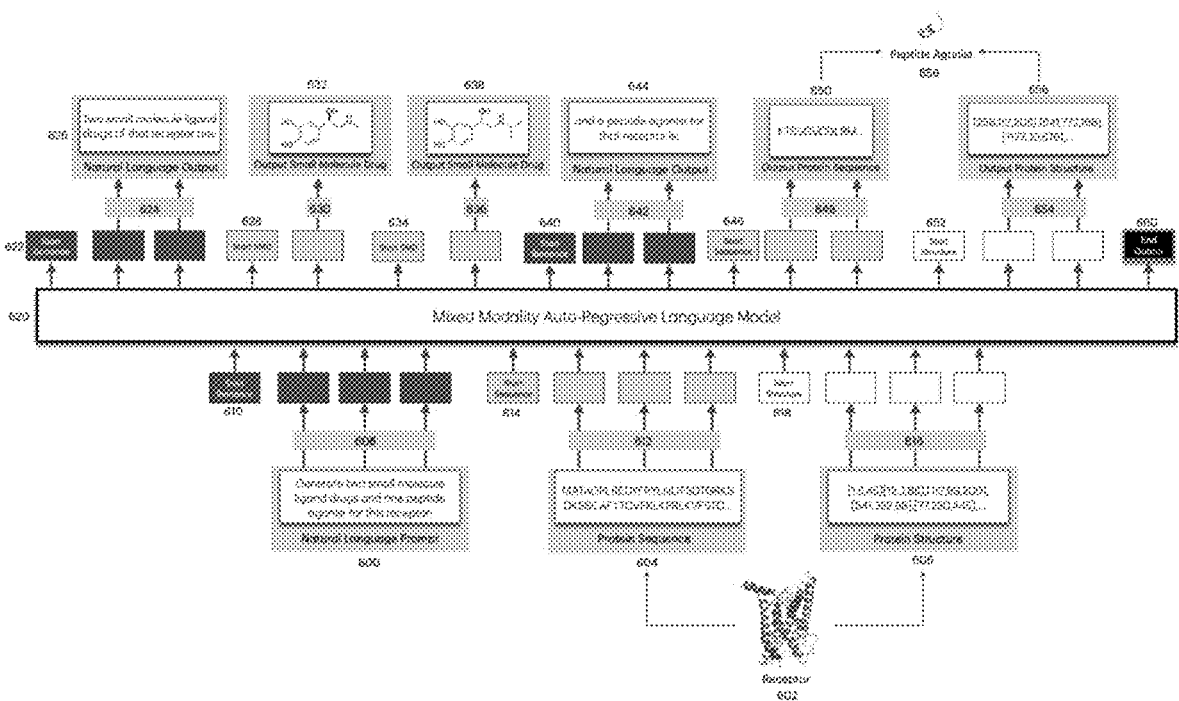
FIG. 6 Illustrative Overview of Inference for an Interleaved Modality Task.

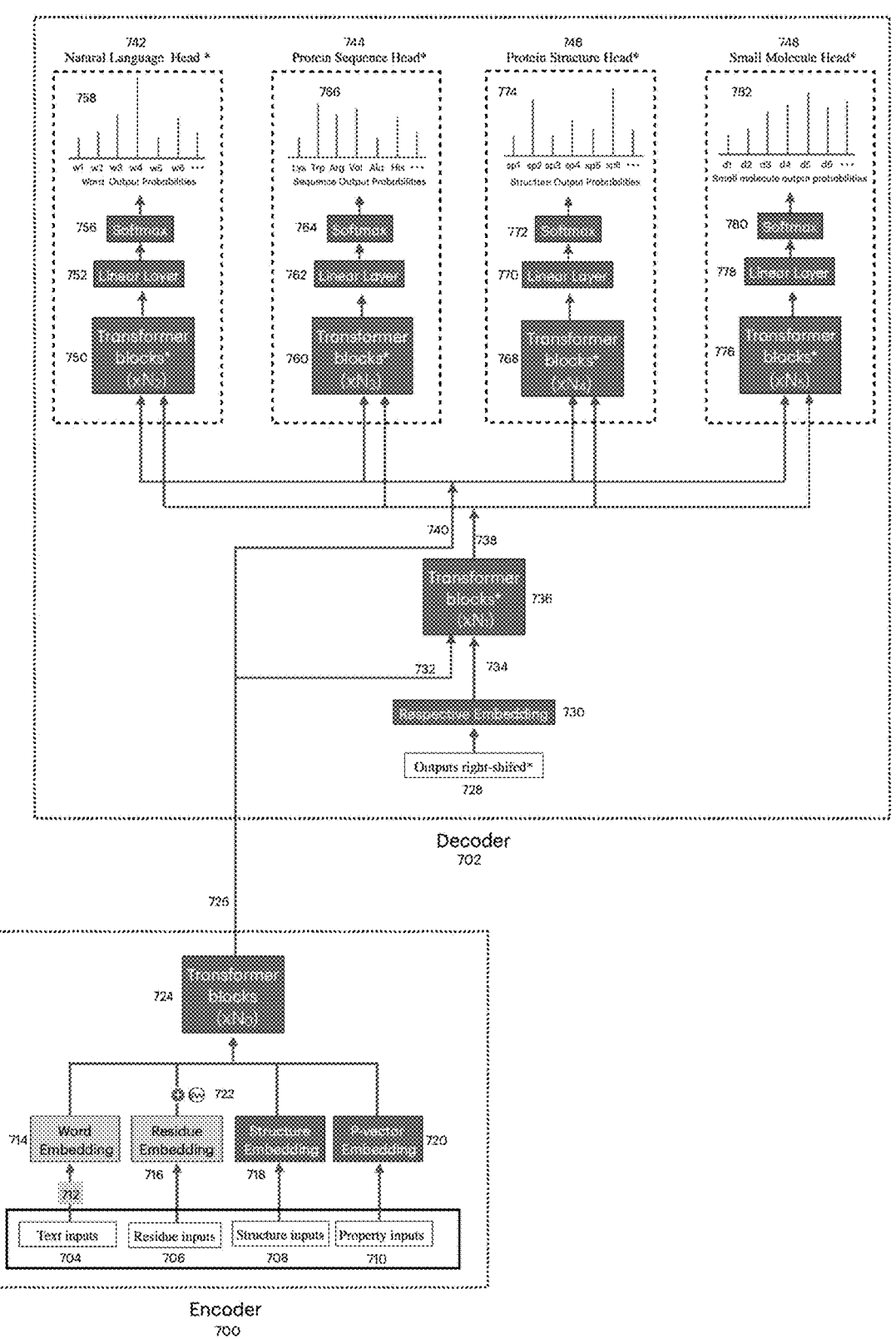
FIG. 7 A Multicapitate Encoder-Decoder Transformer Training Architecture for Mixed Modality Protein and Natural Language Fusion.

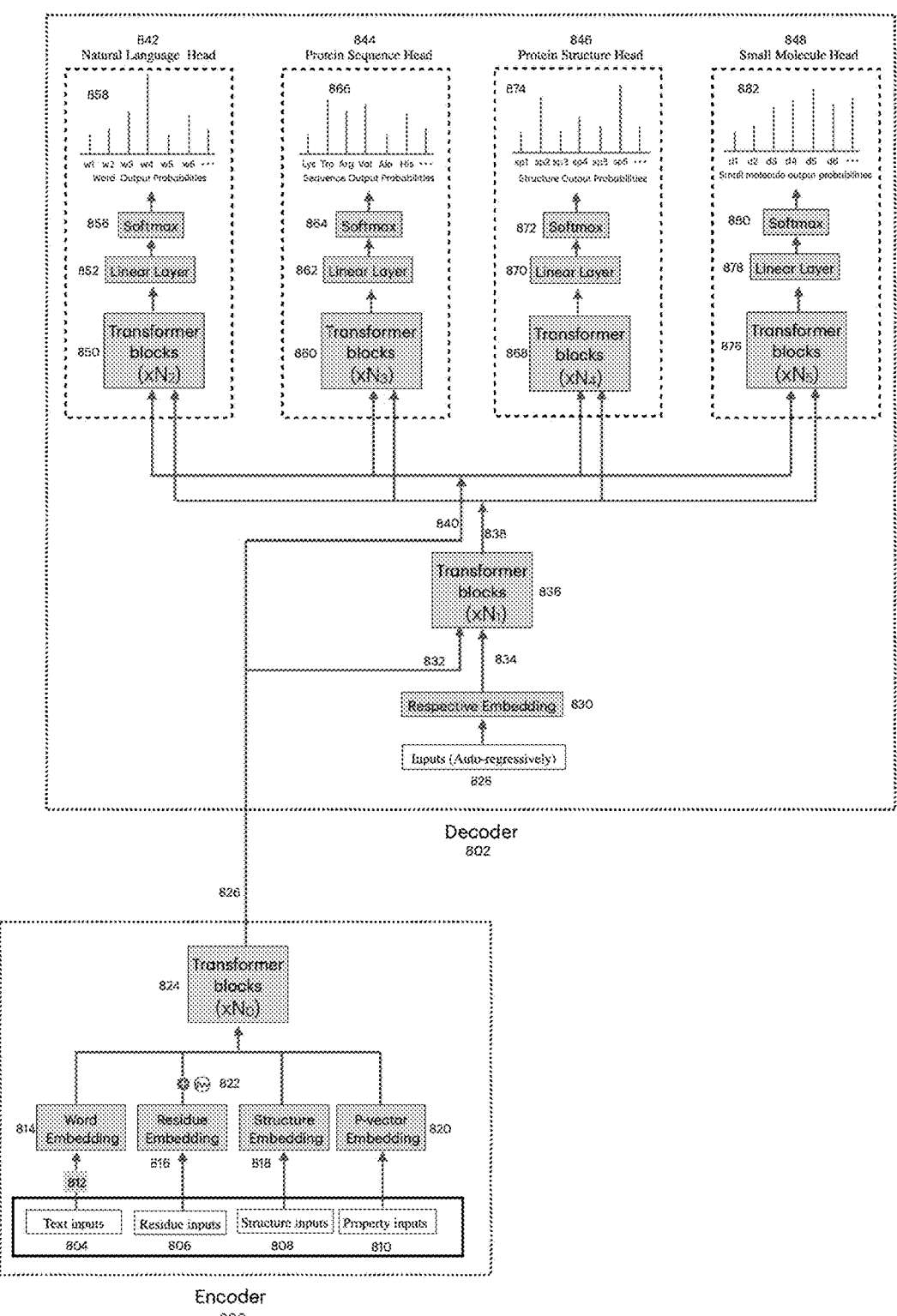
FIG. 8 A Multicapitate Encoder-Decoder Transformer Inference Architecture for Mixed Modality Protein and Natural Language Fusion.

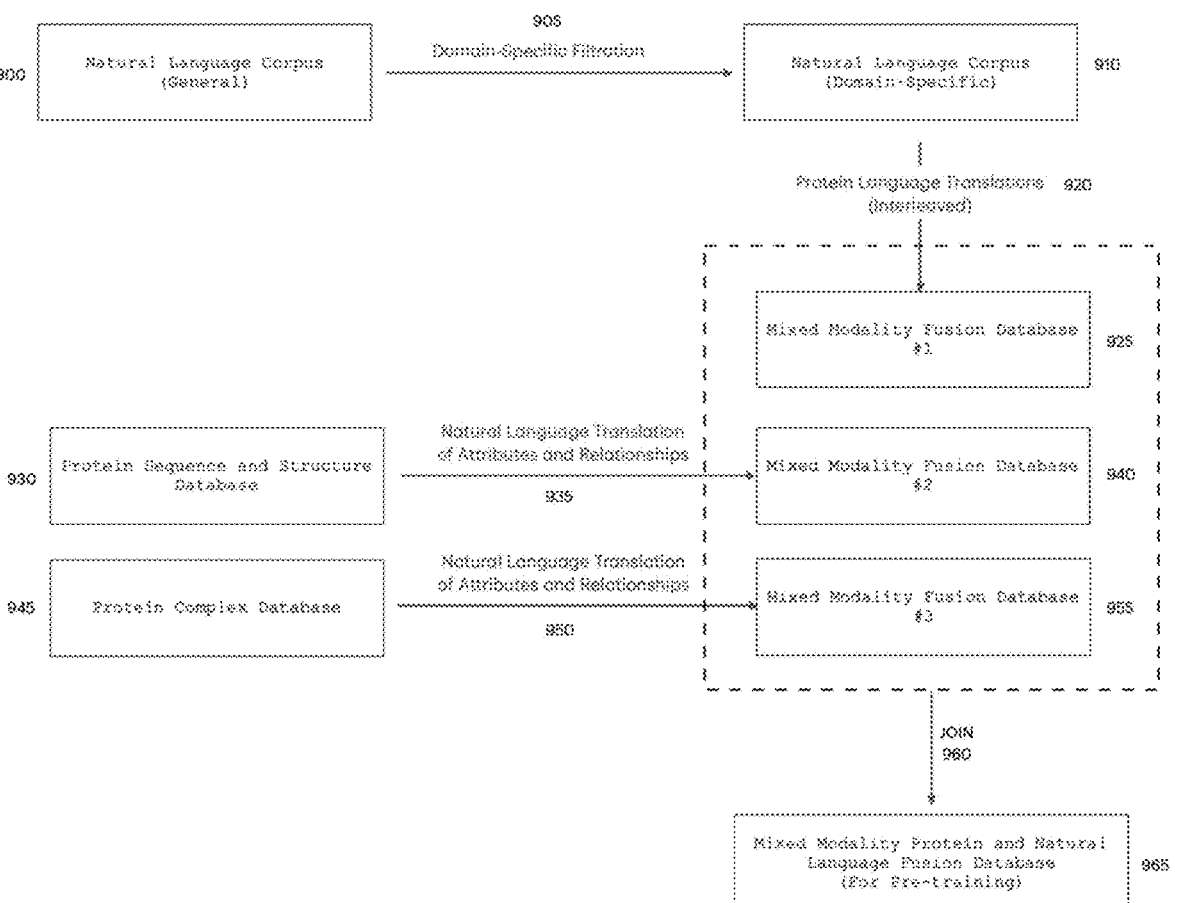
FIG. 9 A Schematic Flow Diagram of Database Crossing to Yield a Mixed Modality
Protein and Natural Language Fusion Database.

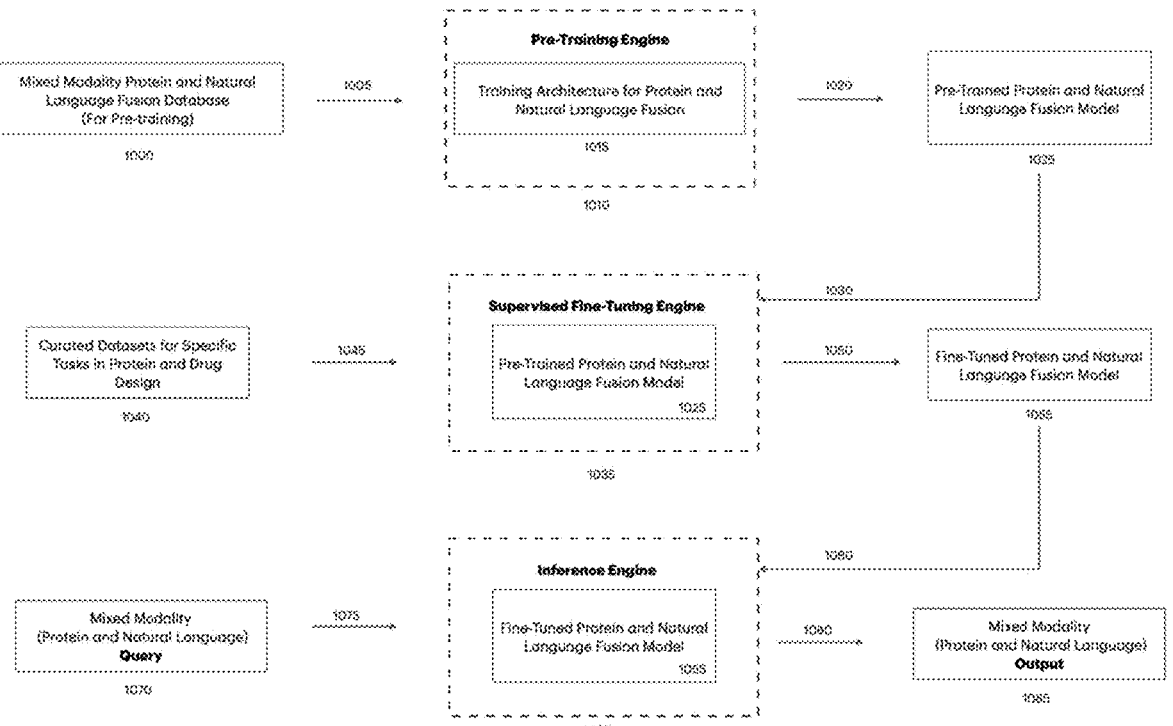
FIG. 10 A Schematic Flow Diagram Overview of Pre-Training, Supervised Fine-Tuning, and Inference Procedures with a Protein and Natural Language Fusion Model.

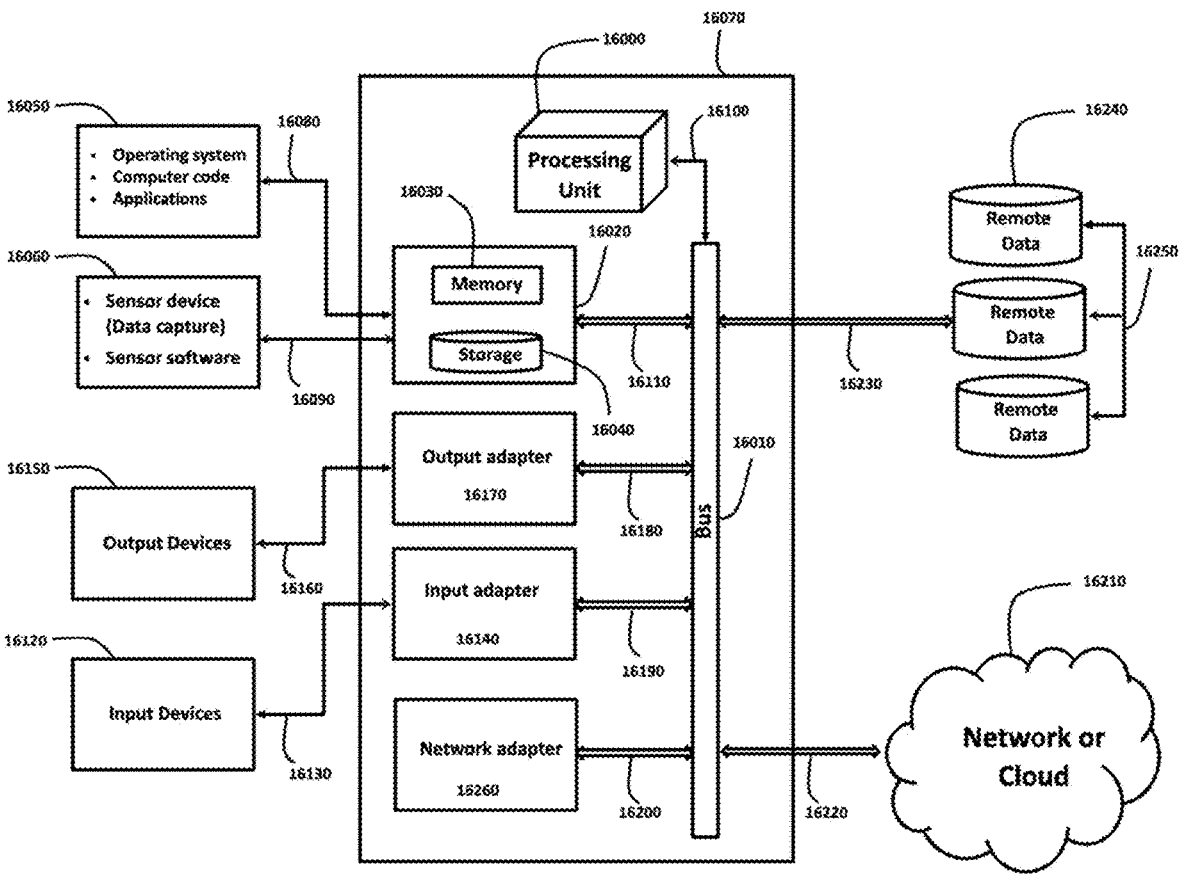
FIG. 11 Computing Environment.

EARLY FUSION OF NATURAL AND PROTEIN LANGUAGE MODELS FOR GENERATIVE AI-BASED PROTEIN AND DRUG DESIGN

INCORPORATION BY REFERENCE OF MATERIAL SUBMITTED ELECTRONICALLY

A separate Sequence Listing XML file of size 8,891 Bytes, created on Mar. 20, 2026, and named "Early_Fusion_Illustrative_00007_19193962.xml" has been submitted and is herein incorporated by reference.

FIELD OF THE INVENTION

The present invention relates generally to Artificial Intelligence (AI) and Machine Learning (ML) methods for protein and drug ligand design, and specifically to learning representation modalities of protein and drug design.

BACKGROUND OF THE INVENTION

Proteins have highly specific and purposeful features including (but by no means limited to) sequence, structure, function, binding partners, interactions, interactors, and properties. Together, these features exquisitely determine the function of the protein. Furthermore, protein function is characterized by highly complex interdependencies that can change with time and with the microenvironment of the protein.

Due to this intrinsically multimodal nature and richness of the protein feature space, it follows that sequence and structure representations alone are unable to adequately represent proteins. Instead, a proper representation of any protein requires a mixture of representation modalities. In particular, the list of admissible representation modalities should include a natural language modality, a sequence modality, and a structure modality.

Much of what is known about proteins to date has been recorded in the natural language representation modality. Though natural language representation may at first glance appear less structured and less definite than protein sequence, for instance; it holds that natural language is able to encode a broader range of protein features. In other words, the natural language representation is both expressive and essential, and is often a critical modal source of the protein information it encodes. Yet natural language is either wholly omitted or is treated as a non-integral external supplement or afterthought by most existing machine learning methods of protein structure and function.

To further highlight the expressivity and essence of the natural language representation, consider the non-limiting example of G-Protein Coupled Receptors (GPCRs). The sequence and structure representations of a GPCR are important parts of the receptor's overall feature representation. However, the sequence and structure representations alone are wholly inadequate for the purpose of understanding the receptor's function and its mechanisms of action; and are also wholly inadequate for the purpose of designing effective drug ligands for the receptor.

Conversely, natural language representation alone would be inadequate for the purpose of protein and drug design and for the purpose of fundamentally understanding protein function and mechanisms of action.

Notably, GPCRs derive their name from a subset of their binding partners, the G-proteins. In particular, a heterotrimeric G-protein complex consisting of alpha, beta, and gamma subunits ($G_\alpha$, $G_\beta$, and $G_\gamma$ respectively), is bound to the GPCR in its inactive state. The GPCRs, also termed seven transmembrane receptors (7TMRs) because they structurally span the cell membrane seven times, have three extracellular loops, three intracellular loops, an extracellular N-terminus, and an intracellular C-terminus, each with a highly specific function.

Upon ligand binding to the binding pocket on the extracellular aspects of the transmembrane domains (or to the extracellular loops), a structural change in the receptor causes the receptor to induce an exchange of guanosine diphosphate (GDP) for guanosine triphosphate (GTP) on the alpha subunit ($G_\alpha$), thereby activating the alpha subunit, causing it to dissociate from the beta-gamma complex, causing it to dissociate from the receptor, and causing it to induce downstream signaling functions such as adenylate cyclase activation. Active adenylate cyclase then converts adenosine triphosphate (ATP) into cyclic adenosine monophosphate (cyclic AMP), an important 2nd-messenger, which in turn activates protein kinase A (PKA).

In this non-limiting example, the highly specific coordinated orchestration of events clearly cannot be captured by the GPCR protein's sequence and structure representations alone. Therefore, for effective design of proteins and drugs, early fusion that includes natural language representation is needed in machine learning methods.

At the same time, it is also true that the end goal in protein design is most often determination of a protein sequence that satisfies certain *desiderata*. Upon determining the sequence, the protein can then be synthesized. However, most existing approaches are inadequate because they exclusively center protein sequence and structure alone, but treat natural language representations—and therefore protein features that are not sequence or structure—as an adjunct or external consideration, as opposed to as a fully integral source of the neural networks' learnings.

In other words, existing approaches to protein representations for machine learning are deficient in that they either omit much of the characteristics of a protein encoded via natural language, or they treat the natural language modality as a non-integral external consideration, not something that is fused into the learnings of the protein representation on an equal footing as protein sequence and structure representations. Here, two representation modalities being on an equal footing means that both are admissible representations in the neural network model architecture and procedures; and are handled in a materially identical or comparable manner architecturally and procedurally.

Here, the term early in early fusion, refers to the chronological and architectural stage of the neural network training process. In the invention disclosed herein, fusion essentially starts from the onset in that the initial training data is of mixed modality, and the neural network weights are shared across modalities very early in the architecture. In the default embodiments of the invention, this fusion which starts early continues essentially throughout the chronological and architectural progression of model training. Of note, however, this is in no way a limitation of the invention, as there are a plurality of means via which training can be conducted and designed both chronologically and architecturally, resulting in a variety of embodiments. For instance, chronologically, a selected subset of the representation modalities may be trained up to a point, before data streams involving other modalities are introduced into the training process. Likewise, architecturally, modality-aware mixture-of-expert approaches may be implemented, wherein the fusion is paused by modality aware routers earlier in the architecture, and then fusioned resumed later (architecturally) by resuming weight sharing. These variant embodiments underscore that there are a plurality of varying degrees and hybrid approaches, which in no way limit the invention.

The representation deficiency that results from lack of an early fusion of modalities and an inadequate representation of natural language, contributes significantly to the high failure rate and high cost of novel drug development efforts. The process of developing a novel drug often costs over $2 billion and more than 10 years to get a single candidate drug through clinical testing phases. Yet despite the exorbitant investment of time and resources, a high percentage of drugs fail in the clinical testing phases. This process and its yield can undoubtedly be significantly improved using machine learning techniques that utilize early fusion of available modalities including natural language, protein sequence, and protein structure, to generate drug candidates for synthesis and clinical testing.

Prior to this disclosure, there were no methods in existence for early fusion of representation modalities of protein features, wherein the allowed modalities include (but are in no way limited to) natural language representation, protein sequence representation, and protein structure representation; and wherein the represented features include (but are in no way limited to) the sequence, structure, function, binding partners, interactions, interactors, and properties of the protein.

Here in the specifications and in the claims, we make a clear distinction between a protein's features and the modalities of representation of the protein's features. They are not the same thing. For instance, a protein's sequence is a feature of the protein, while a sequence representation modality can be used to represent the protein's sequence. Of note, a sequence representation can be used to represent other features of the protein which are not the protein's sequence. For instance, protein's protein binding partners can be represented by a sequence representation. Similarly, a protein's structure is a feature of the protein, while a protein structure representation modality is one way to represent the structure feature. There typically are multiple ways to represent a single feature of a protein. For instance, the structure feature can be represented using coordinate locations of representative atoms in the protein sequence, it may be represented using probability of amino acid locations in voxels, it may be represented using torsion angles, and it may even be expressed using natural language modality.

For most features, only certain representations are capable of properly representing the feature. For instance, choosing to describe a protein's structure exclusively in natural language words is not a computationally effective, efficient, or precise choice available for representing that feature.

The disclosed invention addresses a pressing unmet need and therefore increases the likelihood of successful development of novel effective drugs to treat diseases.

OBJECTS OF THE INVENTION

It is an object of this invention to provide a system, method, and apparatus for early fusion of representation modalities of protein features, wherein the allowed modalities include (but are in no way limited to) natural language representation, protein sequence representation, and protein structure representation; and wherein the represented features include (but are in no way limited to) the sequence, structure, function, binding partners, interactions, interactors, and properties of the protein.

Another object of this invention is to provide a system, method, and apparatus for early fusion of representation modalities of protein features, wherein the allowed modalities include (but are in no way limited to) natural language representation, protein sequence representation, and protein structure representation; and wherein the represented features include (but are in no way limited to) the sequence, structure, function, binding partners, interactions, interactors, and properties of the protein; and wherein the method outputs a protein representation for synthesis or a small molecule drug representation for manufacture.

Another object of this invention is to provide a system, method, and apparatus that accepts an input query of one or more representation modalities and outputs a data stream of one or more representation modalities, wherein the output conditions are prescribed by the input, and wherein the output includes a representation of a protein for synthesis or small molecule drug for manufacture.

Yet other objects, advantages, and applications of the invention will be apparent from the specifications and drawings included herein.

SUMMARY OF THE INVENTION

The invention disclosed herein includes systems, methods, and apparatus for early fusion of representation modalities of protein features, wherein the allowed modalities include (but are in no way limited to) natural language representation, protein sequence representation, and protein structure representation; and wherein the represented features include (but are in no way limited to) the sequence, structure, function, binding partners, interactions, interactors, and properties of the protein; and wherein the method outputs a protein representation for synthesis or a small molecule drug representation for manufacture.

The method comprises receiving a plurality of representations of features of a plurality of proteins, wherein the represented features include (but are in no way limited to) sequence, structure, function, binding partners, interactions, interactors, and properties; and wherein the allowed modalities include (but are in no way limited to) natural language representation, protein sequence representation, and protein structure representation.

The received data is used to train a neural network, wherein in accordance with a supervised learning paradigm, the training objective is for the neural network to learn to yield the corresponding mixed modality output data (label), given a mixed modality input query. Furthermore, an objective of the invention is to output representations of proteins for synthesis or small molecule drugs for manufacture, given mixed modality input queries prescribing desired conditions of the output.

The received data is of mixed modality in the sense that there are more than one allowed representation modalities in which the elements of the data can be represented. By way of example but not limitation, consider the following data instance example drawn from one embodiment of the invention:

Input: "[start-of-sentence] What is an agonist of the following protein?: [start-of-sequence] [ATQMRSCCSSTLLV (SEQ ID NO: 7) . . . ] [end-of-data]"

Output: "[start-of-sentence] One agonist of the protein is: [start-of-sequence] [MATACCSV (SEQ ID NO: 8)]

[start-of-sentence] However, this receptor has several other agonists with varying properties[end-of-data]"

Of note, in this illustrative example, the input data instance consists of a natural language modality part and a protein sequence modality part, while the output data instance consists of a protein sequence modality part between two natural language modality parts.

Similarly, other modalities can be included, and in some embodiments, the sequence length of the input data stream as well as the constituent representation modalities vary by instance. Hence the emphasis on 'allowed' modalities. This flexibility increases the general utility of the invention.

In one embodiment of the invention, the neural network is a transformer. Here in the specifications as well as in the claims, a transformer means a neural network with an attention mechanism. Attention mechanisms are a means of distributing influence to elements (or tokens) of a data stream or context array, when transforming a given element (or token) in that data stream or context array. There are a plurality of ways to implement attention mechanisms. One such way, the scaled dot product attention, is described in the detailed description of the drawings below.

Furthermore, in some embodiments, the neural network is a multicapitate ("multiple headed") transformer in the sense that it has multiple heads, each with its own loss function. In some embodiments, each head of the transformer corresponds to a distinct representation modality. For instance, one head for natural language representation, a different head for protein sequence representation, yet a different head for protein structure representation, and yet a different head for small molecule drug representation, and so on.

In some embodiments, the final output layer of each head yields a probability distribution over the possible values of tokens in a stream expressed in that representation modality. For instance, for the natural language representation, it will be a probability distribution over all the word tokens in the language's vocabulary. For the sequence representation, it will be a probability distribution over all the amino acids, and so on. In addition, the domain of each output probability distribution includes auxiliary tokens such as <start-of-sentence>, <start-of-sequence>, <end-of-output>, etc.

Furthermore, in some embodiments, the transformer is auto-regressive. This allows for the variability in output stream length, as well as the variability in number and types of representation modalities.

Given a dataset consisting of a plurality of representations of features of a plurality of proteins, one can train the neural network in a supervised learning manner, wherein the training objective is for the neural network to yield the mixed modal output stream (training labels) given the mixed modal input stream (training data).

An optimization method such as stochastic gradient descent (or other optimizer) is then used to train the model. The trained model is then used to produce an output stream, which as prescribed by the input query, includes a representation of a protein for synthesis or small molecule drug for manufacture.

Of note, in some embodiments of the invention, the transformer is unicapitate ("single headed"). In such instances wherein the final output layer yields a probability distribution, the distribution is over the union of all the sets of possible values of all the allowed representation modalities. The domain also includes the union of all the auxiliary tokens.

In summary, the invention disclosed herein consists of systems, methods, and apparatus for early fusion of representation modalities of protein features, wherein the allowed modalities include (but are in no way limited to) natural language representation, protein sequence representation, and protein structure representation; and wherein the represented features include (but are in no way limited to) the sequence, structure, function, binding partners, interactions, interactors, and properties of the protein.

The invention consists of several outlined processes below, and their relation to each other, as well as all modifications which leave the spirit of the invention invariant. The scope of the invention is outlined in the claims section.

BRIEF DESCRIPTION OF THE DRAWINGS

In the following detailed description of the invention, we reference the herein listed drawings and their associated descriptions, in which:

FIG. 1 is a 2D representation of a G-Protein Coupled Receptor (GPCR) having the illustrative amino acid sequence of SEQ ID NO: 1.

FIG. 2 is an illustrative overview of the inference process with a mixed-modal early-fusion language model for protein and drug design, wherein the input protein sequence 210 comprises SEQ ID NO: 2 and the output protein sequence 280 comprises SEQ ID NO: 3.

FIG. 3 is an illustrative overview of the training process for a mixed-modal early-fusion language model for protein and drug design, wherein the input protein sequences 325 comprise SEQ ID NO: 4, SEQ ID NO: 5, and SEQ ID NO: 6, and the output protein sequence 380 comprises SEQ ID NO: 3.

FIG. 4 is an illustrative overview of the inference process with a mixed-modal early-fusion language model for small molecule drug design, wherein the input protein sequence 410 comprises SEQ ID NO: 2.

FIG. 5 is an illustrative overview of the pre-training process for a mixed-modal early-fusion language model for small molecule drug design, wherein the input protein sequences 525 comprise SEQ ID NO: 4, SEQ ID NO: 5, and SEQ ID NO: 6.

FIG. 6 is an illustrative overview of inference for an interleaved modality task, wherein the input protein sequence 604 comprises SEQ ID NO: 2 and the output protein sequence 650 comprises SEQ ID NO: 3.

FIG. 7 is a multicapitate encoder-decoder transformer training architecture for mixed modality protein and natural language fusion.

FIG. 8 is a multicapitate encoder-decoder transformer inference architecture for mixed modality protein and natural language fusion.

FIG. 9 is a schematic flow diagram of database crossing to yield a mixed modality protein and natural language fusion database.

FIG. 10 is a schematic flow diagram overview of pre-training, supervised fine-tuning, and inference procedures with a protein and natural language fusion model.

FIG. 11 is a computing environment.

DETAILED DESCRIPTION OF THE PREFERRED EMBODIMENTS

The illustration in FIG. 1 is a two dimensional representation of a G-Protein Coupled Receptor (GPCR) having the illustrative amino acid sequence of SEQ ID NO: 1. The figure exemplifies the diversity of features that can characterize any given protein, such that only a mixture of multiple modalities, including natural language, can sufficiently represent the protein and its associated features; wherein the features we include sequence, structure, function, binding partners, interactions, interactors, and properties.

In the case of GPCRs as exemplified by FIG. 1, there are a number of domains, each with its own characteristic features. For instance, there is an N-terminus 100, an N-terminal tail 175, a C-terminus 105, and a C-terminus tail 180. Furthermore, there are three extracellular loops, i.e. the first extracellular loop (ECL1) 110, the second extracellular loop (ECL2) 115, and the third extracellular loop (ECL3) 120. Similarly, there are three intracellular loops, i.e. the first intracellular loop (ICL1) 160, the second intracellular loop (ICL2) 165, and the third intracellular loop (ICL3) 170.

There are seven transmembrane alpha-helices, hence the name seven transmembrane receptors or 7TMRs, which is an alternate name for the GPCRs. Shown in FIG. 1 are the first transmembrane domain (TM1) 125, the second transmembrane domain (TM2) 130, the third (TM3) 135, fourth (TM4) 140, fifth (TM5) 145, sixth (TM6) 150, and seventh (TM7) 155. The cell membrane 185 is also shown. The transmembrane alpha helices have a tertiary barrel-like arrangement and typically serve—via their extracellular facing side—as the ligand binding site for small molecule drugs, while larger ligands such as peptide ligands bind to the extracellular loops. In the inactive state, the GPCR is bound to a heterotrimeric G-protein. Upon agonist binding, a structural change in the receptor causes a GDP for GTP exchange on the G-protein alpha subunit ($G_\alpha$). This in turn induces dissociation of Ga from the beta-gamma subunit ($G_{\beta\gamma}$); and downstream signaling proceeds.

Such a highly specific orchestrated ensemble of events is typical of cellular processes and cannot be adequately represented computationally without employing a mixture of representation modalities including natural language, protein sequence, protein structure, and small molecule ligand representations.

FIG. 2 is an illustrative overview of an embodiment of the invention wherein an input query consisting of a stream of mixed modality representations of data—including a natural language representation 200, a protein sequence representation 210 (comprising SEQ ID NO: 2), and a protein structure representation 215—is transformed into a mixed modality stream of output data consisting of natural language 265, protein sequence 280 (comprising SEQ ID NO: 3), and protein structure 292 modalities. In particular, the input query requests a peptide agonist for a specified receptor 205, and the output stream provides a representation of a peptide agonist 296 of that receptor.

In the embodiment exemplified in FIG. 2, the natural language prompt 200 is preprocessed 220 by tokenization and embedding. This results in a set of input tokens. A <start-of-sentence> token 225 indicates that the incoming stream of embedding vectors are of a natural language representation modality.

Similarly, the protein sequence input data 210 is preprocessed 230 by embedding, yielding a set of embedding vectors. A <start-of-sequence> token 235 indicates that the incoming stream is of a protein sequence representation modality.

Similarly, the protein structure input data 215 is preprocessed 240 by embedding, yielding a set of embedding vectors. A <start-of-structure> token 245 indicates that the incoming stream is of a protein structure representation modality.

The set of input vector embeddings are served as input into a mixed modality autoregressive language model 250. A <start-of-sentence> token 255 is used to mark the start of the output stream. The output stream's tokens arise one token per iteration, after which the output is joined with the input context array in standard autoregressive language model fashion. The returned output from one iteration is then available for self attention on the next iteration. In this embodiment, the immediate natural language output of the autoregressive language model is detokenized 260 to yield the natural language.

A <start-of-[MODALITY]> token indicates that the incoming stream will be of the specified modality, as such it serves the dual purpose of indicating that the prior modality will pause (or halt). In this example, the <start-of-sequence> token 270 in the output stream indicates that the natural language modality is paused and the protein sequence modality begins. The output of the protein sequence channel can directly be a protein sequence, and therefore in such embodiments, no post processing 275 involving detokenization and unembedding would be needed. Alternatively, other embodiments can involve a detokenization and unembedding post-processing step 275.

In this embodiment (FIG. 2), the <start-of-structure> token 285 indicates a pause in the protein sequence stream and a start of the protein structure stream. The output stream ends altogether upon encountering an <end-of-output> token 294. Together, the output protein sequence representation 280 and structure representation 292 specify a representation of a peptide agonist 296 of the target receptor 205.

FIG. 3 is an illustrative overview of a training process for a mixed-modal early-fusion language model for protein and drug design. This particular example illustrates a mixed modality input query consisting of natural language 310, protein sequence 325 (comprising illustrative sequences including SEQ ID NO: 4, SEQ ID NO: 5, and SEQ ID NO: 6), and protein structure 330 modalities; wherein the associated output stream's training labels 392 are also of mixed modality.

A natural language database 300 including natural language representations of a plurality of features of a plurality of proteins, can be crossed in a number of ways with a protein sequence and structure database 320. For instance, in one embodiment, references to proteins in the natural language database are replaced with the sequence and/or sequence and structure of the respective proteins. This yields a mixed modality database. In addition, relationships between proteins in a protein database are expressed in natural language also yielding a mixed modality database of protein language and natural language.

The resulting mixed modality database obtained by a crossing of a natural language database 300 and a protein database 320 can then be used for pre-training of the mixed modality autoregressive language model 365. In one embodiment, the autoregressive task is next-token prediction. The mixed modality (crossed) database can be partitioned into training and test sets, and training labels 392 used to compute a loss function value. An optimization such as gradient descent can then be applied end-to-end. In some embodiments of the invention, auxiliary tokens such as <start-of-[MODALITY]> tokens are used to indicate the pausing of one modality stream and the start of another. For instance, during a natural language output stream, the emergence of a <start-of-sequence> token 376 signals a pause of the natural language stream and a commencement (or resumption) of the protein sequence stream. An <end-of-output> token 388 indicates the end of the output stream.

In some embodiments, a general natural language database is first topically filtered 305 for relevance before or after modality-crossing of the databases. Next, the respective embeddings are performed for the modalities: here, natural language embedding 335, protein sequence embedding 350, and protein structure embedding 360. The resulting context array of embeddings delineated with <start-of-[MODALITY]> between modal streams, is passed as input into the mixed modality autoregressive language model 365.

In this supervised learning framework, for any given token, all the conditioning as well as the next token to be predicated are known. Hence, the training procedure can be conducted in parallel wherein each token is associated with a distinct thread, and the model weights are shared.

FIG. 4 is an illustrative example overviewing the inference process with a mixed modality early fusion language model for small molecule drug design. The inference procedure of FIG. 4 is materially identical to that described in FIG. 2, and the respective architectures are similar. One difference in these two examples is the input query with which inference is illustrated. In FIG. 4, the input query requests a small molecule drug ligand of the specified target receptor 405, while in FIG. 2, the input query requests a peptide ligand. Consequently, the output here in FIG. 4 is a mixture of natural language modality and a small molecule drug modality, as reflected in the output which is a concatenation of a natural language stream 465 and a small molecule drug 480. In each scenario illustrated in FIG. 2 and FIG. 4 respectively, the architecture of the neural network must be appropriately designed to handle the input and output modalities in the mixture.

FIG. 5 is an illustrative overview exemplifying a pre-training procedure of a mixed modality fusion language model for small molecule drug design. The pre-training procedure of FIG. 5 is materially identical to that described above for FIG. 3. The respective architectures are similar. As in the prior comparison, one difference in these two examples is the input query with which the forward pass is illustrated. In FIG. 5, the input query requests a small molecule drug ligand of a specified target receptor sourced from the receptor database 520, while in FIG. 3, the input query requests a peptide ligand. Consequently, the output here (FIG. 5) is a mixture of natural language modality and a small molecule drug modality, as reflected in the output which is a concatenation of a natural language stream 580 and a small molecule drug 588.

FIG. 6 is an illustrative example overviewing inference for an interleaved modality task. The input query consists of three modalities: natural language, protein sequence 604 (comprising SEQ ID NO: 2), and protein structure. The natural language input stream 600, queries for two small molecule drugs and one peptide agonist. The query subject, a target receptor 602, is bimodally specified via a protein sequence stream 604 and a protein structure stream 606. The natural language part 600 of the input array says "Generate two small molecule ligand drugs and one peptide agonist for this receptor:." The mixed modality autoregressive language model 620 must have been trained adequately enough to output the illustrative stream which semantically satisfies the input query's request. In particular, the autoregressively generated output stream begins with a <start-of-sentence> 622, followed by natural language output stream 626. Next a <start SMD> token 628 signals a pause in the natural language stream and the start of the SMD stream. Next an SMD 632 is output followed by another <start SMD> token 634 closing the prior SMD stream and commencing the next one in accordance with the input query request. The next SMD 638 is output followed by another <start-of-sentence> token 640 indicating the start of a natural language stream 644. This is followed by a <start-of-sequence> token 646 indicating the start of the sequence stream 650 (comprising SEQ ID NO: 3 of the peptide agonist. This is followed by a <start-of-structure> token 652 signaling for the end of the output sequence stream and the start of the protein structure stream 656. Together, the output protein sequence stream and its associated protein structure stream constitute an output representation of the peptide agonist 658. Finally, an <end-of-output> token 660 signals for a halt of the output stream.

FIG. 7 is an illustrative example of a multicapitate encoder-decoder transformer training architecture for mixed modality protein and natural language fusion. In this embodiment, the encoder 700 can accept a concatenated array of input data of a mix of modalities. In this particular example, the input modalities include natural language (or "text") 704, protein sequence (or "residues") 706, structure inputs 708, and property inputs 710, which are a prespecified data structure (a p-vector) encoding a pre-specified set of properties.

The input data for natural language 704, sequence 706, structure 708, and property 710, are each passed through their respective embeddings, i.e. word embedding 714, residue embedding 716, structure embedding 718, and p-vector embedding 720. The concatenated array of output embedding vectors encodes an input query whose response is a mixed modality output stream at the terminus of the decoder 702. The mixed modality output stream is measured against the corresponding training label for the input context array. In this particular embodiment, the multicapitate ("multiple headed") architecture consists of one head per output modality: a natural language head 742, a protein sequence head 744, a protein structure head 746, and a small molecule head 748. Since this is a training architecture, each of the respective output heads are associated with a loss function computation, indicated in the figure by an asterisk.

Back to describing the encoder 700: Each modality of the input data array has a respective embedding. The natural language inputs are first tokenized 712 prior to being passed into its embedding, the word embedding 714. The amino acid sequences are acted on by the respective embedding, the residue embedding 716; the structure inputs are acted on by a structure embedding, and the pre-specified property inputs are acted on by the p-vector embedding. The residue embedding vector is imprinted with a positional encoding 722.

The embedding vector array is then passed into a set of repeating transformer blocks 724. The number of repeats No is a design hyperparameter of the architecture. Within each transformer block is a self-attention mechanism. The transformed output array from the encoder is then passed 726 into the decoder for cross-attention.

The encoder 700 can accept a structure input vector 708 into the structure embedding 718. The structure input vector is a vector of structure parameters. In one embodiment, it is of fixed length, L, and zero padding is used for target proteins whose structure parameters are represented by a vector of smaller length than the fixed length, L. The fixed length, L, is a hyperparameter.

The structure embedding 718 is a weight matrix, $W_s$, which the structure input vector, x, 708 multiplies to yield the structure embedding vector, s, as follows:

$$W_s x = s$$

where $W_s$ is an m×L matrix, L is the fixed length of the structure input vector, and m is the length of the amino acid residue embedding vectors, the length of the property (p-vector) embedding vectors, and the length of the word embedding vectors. They all have the same length m. Both m and L are hyperparameters of the model.

The encoder 700 can also accept a protein's amino acid residue inputs 706, which can be in the form of one-hot-encoder vectors which are passed into the residue embedding 716, wherein the residue embedding is itself a trained neural network. A position encoding 722 can be added to the output residue embedding vectors to imprint a signal of sequence position on the respective residue embeddings.

A variable length array of vectors consisting of embedding vector(s)—wherein each vector is from one of the represented modalities—is passed as input into the transformer block 724. The first layer of the transformer block is an attention layer.

Here and in the claims, transformer means a neural network with an attention mechanism. There are a plurality of ways to implement attention mechanisms. In one embodiment, attention layers consist of three types of weight matrices: a query weight matrix, $W_q$, a key weight matrix, $W_k$, and a value weight matrix, Wv. Each of the embedding vectors in the array are then multiplied by each of the three matrices to obtain respective queries, keys, and values, as follows:

$$W_q u = q$$
$$W_k u = k$$
$$W_v u = v$$

where u is an embedding vector (i.e. in this embodiment u is a word embedding vector, residue embedding vector, structure embedding vector, or p-vector embedding vector).

For each embedding vector in the array, the dot product of its respective query vector is taken with the key vectors of all token representations in the context array. Next, a softmax operation is done on the resulting array to yield a probability distribution for each token. Next, for each token, a linear combination of values v is taken wherein the coefficient of each value is the respective probability (i.e. attention weight). The output of this linear combination is then taken as the token's respective output into the next layer of the transformer. This is done for each token in the encoder, therefore the length of the input array and the length of the output array from this attention layer are the same. Given the ith token, its corresponding coefficient associated with the jth token can be denoted $c_{ij}$ and is given by, $$c_{ij} = \frac{e^{<qi,kj>}}{\sum_p e^{<qi,kp>}}$$

The attention layer output of the ith token can be denoted $o_i$ and is then given by, $$o_i = \sum_j c_{ij} v_j$$

In some embodiments, the dot product $<q_i, k_j>$ can be scaled by a variance factor.

The array of outputs $o_i$ are then passed into a normalization layer. Furthermore, a copy of the input array which was passed into the attention layer is passed into and added to a normalization layer, skipping the attention layer. This skip connection serves to preserve the pre-attention layer character signal thereby enhancing available signals for learning.

The output from the Add skip & Norm layer is passed into a feed forward neural network layer and from there into another Add skip & Norm layer. The encoder transformer block 724 of "attention→add skip & norm→feed forward→Add skip & norm" is repeated No number of times where No is a hyperparameter of the model architecture.

Per autoregression, the inputs 728 into the decoder are the right-shifted outputs of the decoder. Here, the asterisk indicates that this can be run in parallel, one thread per token, since all conditioning tokens and the next-token (i.e. the label) are all known. At each iteration of the autoregression, the input is acted on by the respective embedding 730 to yield an embedding vector which is passed into the set of repeating transformer blocks 736. The transformer blocks of the decoder are as described earlier for the encoder, with the exception of 'masked attention.' Unlike the encoder, here in the decoder, in this embodiment, each transformer block consists of a 'masked attention' layer simply implementing the right-shifting in that the next token to be predicted as well as all future tokens are kept masked from the prediction algorithm under training. The current input token and all preceding tokens, however, are visible to the prediction algorithm under training, and furthermore are used as the context array elements for self-attention. The output of the self-attention layer passes into an add-skip-norm layer and onwards into a cross-attention layer. This input is the subject token of the cross-attention layer, while the encoder's final layer output is the remainder of the context array for cross-attention.

The number of repeats $N_1$ of the decoder body transformer block 736 is a design hyperparameter of the model. The resulting final output of the repeating sequence of decoder body transformer blocks is passed 738 into each head of the decoder as shown. In addition, the encoder's final layer output is also passed 740 into each of the decoder's heads for cross-attention.

The respective number of repeats—$N_2$, $N_3$, $N_4$, $N_5$—of the decoder head transformer blocks are also design hyperparameters of the model. Furthermore, they can be zero, in that some heads may have no transformer blocks.

The final output layer of the decoder head transformer blocks is passed into a linear layer which spans the possible values of each respective head. E.g. in the case of the natural language head it spans the language's vocabulary; in the case of the sequence head, it spans the set of amino acids; in the case of small molecule drug (SMD) head, it spans a library of SMDs. In each case the domain also includes auxiliary tokens such as <start-of-[MODALITY]> tokens or <end-of output> tokens.

The linear layer output in turn passes into a softmax layer, yielding a probability distribution over the possible values of the respective heads including auxiliary tokens such as <start-of-[MODALITY]> tokens or <end-of output> tokens.

In the training architecture, optimization is performed to update the weights using optimization methods such as gradient descent for example. Other optimization methods can be used, such as genetic algorithm, particle swarm, simulated annealing, amongst others.

FIG. 8 is a multicapitate encoder-decoder transformer inference architecture for mixed modality protein and natural language fusion. In this case, the neural network has already been trained, and is being used for inference.

One set of differences between the training (FIG. 7) and the inference (FIG. 8) architectures stems from parallelizeability, in that the training architecture is parallelizable while the inference architecture is not parallelizable in the same way. In particular, in the training architecture, since the labels and inputs are all known during training, there is a need for masking in the decoder's attention layer. However, in the inference architecture, the output token generation must be done sequentially, hence no masking is needed.

The other set of differences between the training (FIG. 7) and the inference (FIG. 8) architectures, stems from the basic purpose of training vs inference. In particular, since inference architecture does not involve training, the sequence and structure heads are not associated with a loss function. Instead, they simply terminate with their respective output probabilities 858, 866, 874, and 882. The weights are learnable only during training (FIG. 7) but are frozen during inference (FIG. 8).

The embodiments of the invention exemplified in FIG. 7 and FIG. 8 are multicapitate in that the decoder has multiple heads, each with its own loss function. In other embodiments of the invention, however, the decoder has only a single head. In such embodiments, the linear layer spans the set of possible values of each of the represented modalities. For instance, the set would contain all the words in the natural language vocabulary as well as all the amino acids (e.g. 20 amino acids in humans), as well as all the small molecule drugs in a selected library, as well as all the allowed protein structure representation values, as well as all the auxiliary tokens such as <start-of-sentence>, <start-of-structure>, <start-of-SMD>, <end-of-output>, etc. The single unified probability distribution would be sampled at each iteration of the autoregression, and the most probable token would be selected. In the unicapitate embodiments, the auxiliary tokens serve the same function as in the multicapitate embodiments. The neural network supervised learning training process teaches the neural network to perform as instructed by the output stream data labels.

FIG. 9 is a schematic flow diagram of database crossing to yield a mixed modality protein and natural language fusion database. In this embodiment, the process starts by receiving a natural language corpus 900, wherein the corpus is large, representative, and general. Next, a domain-specific filtration 905 is performed and yields a domain-specific natural language corpus 910. The extent of the domain-specific filtration 905 is a tunable design factor of the system. In some embodiments, the filtration schema includes selecting data units that contain certain search terms.

The domain-specific natural language corpus 910 is then transformed by interleaving it with protein language translations 920, wherein anywhere a specific protein is referenced in the corpus, the sequence representation of that protein as well as its structure representation (if available) are used as replacement for the natural language representation of that protein in the corpus. This translation process 920 results in a mixed modality fusion database 925 consisting of natural language, protein sequence, and protein structure representations. The source of the sequence and structure translations are protein sequence and structure databases 930.

The protein sequence and structure databases 930 are themselves interleaved with natural language translations of their attributes and relationships 935. This translation yields another mixed modality fusion database 940, consisting of natural language, protein sequence, and protein structure representations. In addition, protein complex databases 945 are also interleaved with natural language translations of their attributes and representations 950, also yielding a mixed modality fusion database 955.

The three types of mixed modality databases derived via the above described database crossings are then joined together 960, yielding a larger combined fusion database 965 that is then used for pre-training as previously described.

FIG. 10 is a schematic flow diagram overview of pre-training, supervised fine-tuning, and inference procedures of a protein and natural language fusion model. A mixed modality protein and natural language fusion database 1000 such as whose derivation was exemplified in FIG. 9 above, is used for pre-training. An example of a pre-training procedure and architecture 1015 was earlier described in FIG. 7. The pre-training engine 1010 uses the pre-training procedure and fusion database 1000 to pre-train the mixed modality fusion model 1015. This yields a pre-trained protein and natural language fusion model 1025.

Next, curated datasets for specific tasks in protein and drug design 1040 are passed into a Supervised Fine-Tuning (SFT) engine 1035 which performs supervised fine-tuning on the pretrained protein and natural language fusion model 1025. SFT is a form of transfer learning in which a pre-trained model is further trained by starting out with the pre-trained weights instead of randomly initialized weights. SFT in particular uses curated datasets that teach the pre-trained model a specific customized task. The resulting fine-tuned protein and natural language fusion model 1055 is the core component of the inference engine 1065. The inference engine accepts mixed modality (protein and natural language) queries 1070 as input, and outputs mixed modality (protein and natural language) responses to the input queries. By way of non-limiting example, depending on the input query, the output response can include a requested protein sequence and structure representation, which can then be synthesized. By way of non-limiting example, the output may be a peptide ligand representation for synthesis, a small molecule drug for manufacture, or an antibody for a given antigen, wherein the antibody is a monoclonal antibody (mAb) drug for synthesis or an antibody drug conjugate (ADC) for synthesis. These examples in no way limit the range of possible output types and their uses.

Ones with ordinary skill in the art will recognize that the invention disclosed herein can be implemented over an arbitrary range of computing configurations. We will refer to any instantiation of these computing configurations as the computing environment. An illustrative example of a computing environment is depicted in The Computing Environment FIG. Examples of computing environments include but are not limited to desktop computers, laptop computers, tablet personal computers, mainframes, mobile smart phones, smart television, programmable hand-held devices and consumer products, distributed computing infrastructures over a network, cloud computing environments, or any assembly of computing components such as memory and processing—for example.

As illustrated in The Computing Environment FIG, the invention disclosed herein can be implemented over a system that contains a device or unit for processing the instructions of the invention. This processing unit 16000 can be a single core central processing unit (CPU), multiple core CPU, graphics processing unit (GPU), multiplexed or multiply-connected GPU system, or any other homogeneous or heterogeneous distributed network of processors.

In some embodiment of the invention disclosed herein, the computing environment can contain a memory mechanism to store computer-readable media. By way of example and not limitation, this can include removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer.

As depicted in The Computing Environment FIG, the computing environment can include a system memory 16030 which can be volatile memory such as random access memory (RAM) and may also include non-volatile memory such as read-only memory (ROM). Additionally, there typically is some mass storage device 16040 associated with the computing environment, which can take the form of hard disc drive (HDD), solid state drive, or CD, CD-ROM, blu-ray disc or other optical media storage device. In some other embodiments of the invention the system can be connected to remote data 16240.

The computer readable content stored on the various memory devices can include an operating system, computer codes, and other applications 16050. By way of example not limitation, the operating system can be any number of proprietary software such as Microsoft windows, Android, Macintosh operating system, iphone operating system (iOS), or Linux commercial distributions. It can also be open source software such as Linux versions e.g. Ubuntu. In other embodiments of the invention, data processing software and connection instructions to a sensor device 16060 can also be stored on the memory mechanism. The procedural algorithm set forth in the disclosure herein can be stored on—but not limited to—any of the aforementioned memory mechanisms. In particular, computer readable instructions for training and subsequent image classification tasks can be stored on the memory mechanism.

The computing environment typically includes a system bus 16010 through which the various computing components are connected and communicate with each other. The system bus 16010 can consist of a memory bus, an address bus, and a control bus. Furthermore, it can be implemented via a number of architectures including but not limited to Industry Standard Architecture (ISA) bus, Extended ISA (EISA) bus, Universal Serial Bus (USB), microchannel bus, peripheral component interconnect (PCI) bus, PCI-Express bus, Video Electronics Standard Association (VESA) local bus, Small Computer System Interface (SCSI) bus, and Accelerated Graphics Port (AGP) bus. The bus system can take the form of wired or wireless channels, and all components of the computer can be located remote from each other and connected via the bus system. By way of example and not of limitation, the processing unit 16000, memory 16020, input devices 16120, output devices 16150 can all be connected via the bus system. In the representation depicted in The Computing Environment FIG, by way of example not limitation, the processing unit 16000 can be connected to the main system bus 16010 via a bus route connection 16100; the memory 16020 can be connected via a bus route 16110; the output adapter 16170 can be connected via a bus route 16180; the input adapter 16140 can be connected via a bus route 16190; the network adapter 16260 can be connected via a bus route 16200; the remote data store 16240 can be connected via a bus route 16230; and the cloud infrastructure can be connected to the main system bus vis a bus route 16220.

In some embodiment of the invention disclosed herein, The Computing Environment FIG illustrates that instructions and commands can be input by the user using any number of input devices 16120. The input device 16120 can be connected to an input adapter 16140 via an interface 16130 and/or via coupling to a tributary of the bus system 16010. Examples of input devices 16120 include but are by no means limited to keyboards, mouse devices, stylus pens, touchscreen mechanisms and other tactile systems, microphones, joysticks, infrared (IR) remote control systems, optical perception systems, body suits and other motion detectors. In addition to the bus system 16010, examples of interfaces through which the input device 16120 can be connected include but are by no means limited to USB ports, IR interface, IEEE 802.15.1 short wavelength UHF radio wave system (bluetooth), parallel ports, game ports, and IEEE 1394 serial ports such as FireWire, i.LINK, and Lynx.

In some embodiment of the invention disclosed herein, The Computing Environment FIG illustrates that output data, instructions, and other media can be output via any number of output devices 16150. The output device 16150 can be connected to an output adapter 16170 via an interface 16160 and/or via coupling to a tributary of the bus system 16010. Examples of output devices 16150 include but are by no means limited to computer monitors, printers, speakers, vibration systems, and direct write of computer-readable instructions to memory devices and mechanisms. Such memory devices and mechanisms can include by way of example and not limitation, removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer. In addition to the bus system 16010, examples of interfaces through which the output device 16150 can be connected include but are by no means limited to USB ports, IR interface, IEEE 802.15.1 short wavelength UHF radio wave system (bluetooth), parallel ports, game ports, and IEEE 1394 serial ports such as FireWire, i.LINK, and Lynx.

In some embodiment of the invention disclosed herein some of the computing components can be located remotely and connected to via a wired or wireless network. By way of example and not limitation, The Computing Environment FIG shows a cloud 16210 and a remote data source 16240 connected to the main system bus 16010 via bus routes 16220 and 16230 respectively. The cloud computing infrastructure 16210 can itself contain any number of computing components or a complete computing environment in the form of a virtual machine (VM). The remote data source 16240 can be connected via a network to any number of external sources such as NMR spectrometry devices, X-ray diffraction devices, electron microscopes, imaging devices, imaging systems, or imaging software.

In some embodiment of the invention disclosed herein, a sensor system 16060 which captures and pre-processes data is attached directly to the system. For example, this may be an electron microscope (and associated image processing software); it may be a camera in the case of an imaging system, say for processing distance map photographs; or it may be an X-ray crystallography machine or an NMR spectrometer (and associated software), excetera. Stored in the memory mechanism—16020, 16240, or 16210—are machine learning models, algorithms, and data products developed according to the procedures set-forth herein. Computer-readable instructions are also stored in the memory mechanism, so that upon command, protein structure representation data, its substrates and associated data can be captured or can be received over a network from a remote or local previously collated database. This transmission of data can be done over a wired or wireless network as previously detailed, as the source and/or recipient of the data output can be at a remote location.

The objects set forth in the preceding are presented in an illustrative manner for reason of efficiency. It is hereby noted that the above disclosed methods and systems can be implemented in manners such that modifications are made to the particular illustration presented above, while yet the spirit and scope of the invention is retained. The interpretation of the above disclosure is to contain such modifications, and is not to be limited to the particular illustrative examples and associated drawings set-forth herein.

Furthermore, by intention, the following claims encompass all of the general and specific attributes of the invention described herein; and encompass all possible expressions of the scope of the invention, which can be interpreted—as pertaining to language—as falling between the aforementioned general and specific ends.

---

SEQUENCE LISTING

```
Sequence total quantity: 8
SEQ ID NO: 1             moltype = AA  length = 223
FEATURE                  Location/Qualifiers
source                   1..223
                         organism = synthetic construct
                         mol_type = protein
                         note = Illustrative fictional GPCR amino acid sequence
SEQUENCE: 1
STAPLSTVCA GAPNPDETWE QGQKRDPAGA SAYCEPAGGR KPELSTALIV APASGATVIG   60
FRHLHSVLRN VLTALIAATV PAAAAAAACA AAAAAAAYCG AVFSRAYDRY ALLFSVDEWA  120
RIGVLASTAA FACAAAAAAP TFAYLFRGIA NLVSTAAVAF ICSYLADAAA AAAAAAAAAA  180
ALSICYFTLA GEVFNCEKCP PAGATMRSDP RKGTPQAWRC GMS                   223

SEQ ID NO: 2             moltype = AA  length = 50
FEATURE                  Location/Qualifiers
source                   1..50
                         organism = synthetic construct
                         mol_type = protein
                         note = Illustrative fictional protein sequence used as
                          input query
SEQUENCE: 2
MATAGPLRED YFRYLNLIFS DTGRKSDKSS CAFYTCVFKL KPRLKVFSTC                50

SEQ ID NO: 3             moltype = AA  length = 11
FEATURE                  Location/Qualifiers
source                   1..11
                         organism = synthetic construct
                         mol_type = protein
                         note = Illustrative fictional output protein sequence
SEQUENCE: 3
KTSSGVCDLR M                                                          11

SEQ ID NO: 4             moltype = AA  length = 6
FEATURE                  Location/Qualifiers
source                   1..6
                         organism = synthetic construct
                         mol_type = protein
                         note = Illustrative fictional partial protein sequence used
                          in training data
SEQUENCE: 4
WATAGP                                                                6

SEQ ID NO: 5             moltype = AA  length = 6
FEATURE                  Location/Qualifiers
source                   1..6
                         organism = synthetic construct
                         mol_type = protein
                         note = Illustrative fictional partial protein sequence used
                          in training data
SEQUENCE: 5
FSVRED                                                                6

SEQ ID NO: 6             moltype = AA  length = 5
FEATURE                  Location/Qualifiers
source                   1..5
                         organism = synthetic construct
                         mol_type = protein
```

-continued

```
                          note = Illustrative fictional partial protein sequence used
                            in training data
SEQUENCE: 6
WQLNL                                                                     5

SEQ ID NO: 7              moltype = AA  length = 14
FEATURE                   Location/Qualifiers
source                    1..14
                          organism = synthetic construct
                          mol_type = protein
                          note = Illustrative fictional partial protein sequence used
                            in input example
SEQUENCE: 7
ATQMRSCCSS TLLV                                                          14

SEQ ID NO: 8              moltype = AA  length = 8
FEATURE                   Location/Qualifiers
source                    1..8
                          organism = synthetic construct
                          mol_type = protein
                          note = Illustrative fictional partial protein sequence used
                            in output example
SEQUENCE: 8
MATACCSV                                                                  8
```

What is claimed:

1. A method; comprising:

a) receiving, at a processor, a dataset consisting of a plurality of representations of features of a plurality of proteins:

i) wherein respective modalities of the representations include:

(1) natural language representation modality; and (2) sequence representation modality; and ii) wherein the represented features include one or more of sequence, structure, function, interactions, inter-actors, binding partners, attributes, and properties;

b) using the dataset to train a neural network:

i) wherein the neural network is configured to accept as input data, a query consisting of one or more of the respective modalities, and to yield as output data, a response to the query, wherein the response comprises of one or more of the respective modalities;

ii) wherein the neural network has multiple heads, each with its own loss function; and iii) wherein the neural network heads include one head for natural language representation output and a different head for protein sequence representation output; and c) using the trained neural network to generate a representation of an output protein, in response to a query specifying conditions on the protein; and d) synthesizing the protein.

2. The method of claim 1, further comprising synthesizing the protein.

3. The method of claim 1, wherein in addition to the natural language head and the protein sequence head, the neural network also has a different head for a protein structure representation modality.

4. The method of claim 3, wherein the neural network is a transformer.

5. The method of claim 4, wherein the transformer is autoregressive.

6. The method of claim 5, wherein for each respective head of the transformer, final output is a probability distribution over a set of possible values at that head.

7. The method of claim 6, wherein a query specifies a target receptor and requests a peptide ligand of the receptor;

and wherein a representation of a peptide ligand of the specified target receptor is generated by the trained neural network.

8. The method of claim 7, further comprising:

a) generating, using a given query a representation of a peptide ligand by randomly sampling an output probability distribution of an active head, at each iteration of an autoregression process;

b) storing the resultant peptide ligand representation in memory;

c) using the given query, repeating the random-sampling-based generation process a plurality of times, each yielding a candidate peptide ligand;

d) assessing interaction, efficacy, and properties of each candidate ligand with the target receptor;

e) selecting, based on the assessment, a candidate ligand; and f) synthesizing the selected ligand.

9. The method of claim 8, wherein for each of the following modalities: natural language, protein sequence, and protein structure, an input embedding used for input data of each respective modality is distinct from an input embedding used for input data of any of the other modalities.

10. A method; comprising:

a) receiving, at a processor, a dataset consisting of a plurality of representations of features of a plurality of proteins:

i) wherein respective modalities of the representations include:

(1) natural language representation modality, (2) sequence representation modality, (3) structure representation modality, and (4) small molecule drug representation modality; and ii) wherein the represented features include one or more of sequence, structure, function, interactions, inter-actors, binding partners, attributes, and properties;

b) using the dataset to train a neural network:

i) wherein the neural network is configured to accept as input data, a query consisting of one or more of the respective modalities, and to yield as output data, a response to the query, wherein the response comprises of one or more of the respective modalities, ii) wherein the neural network has multiple heads, each with its own loss function, and iii) wherein the neural network heads include one head for natural language representation output, a different head for protein sequence representation output, a different head for protein structure representation output, and a different head for small molecule drug representation output;

c) using the trained neural network to generate a representation of an output small molecule drug, in response to a query specifying conditions on the small molecule drug; and d) manufacturing the small molecule drug.

11. The method of claim 10, further comprising manufacturing the small molecule drug.

12. The method of claim 11, wherein the neural network is a transformer.

13. The method of claim 12, wherein the transformer is autoregressive.

14. The method of claim 13, wherein for each respective head of the transformer, final output is a probability distribution over a set of possible values at that head.

15. The method of claim 14, wherein a query specifies a target receptor and requests a small molecule drug ligand of the receptor; and wherein a representation of a small molecule drug ligand of the specified target receptor is generated by the trained neural network.

16. The method of claim 15, further comprising:

a) generating, using a given query a representation of a small molecule drug ligand by randomly sampling an output probability distribution of an active head, at each iteration of an autoregression process;

b) storing the resultant small molecule drug ligand representation in memory;

c) using the given query, repeating the random-sampling-based generation process a plurality of times, each yielding a candidate small molecule drug ligand;

d) assessing interaction, efficacy, and properties of each candidate ligand with the target receptor;

e) selecting, based on the assessment, a candidate ligand; and f) synthesizing the selected ligand.

17. The method of claim 16, wherein for each of the following modalities: natural language, protein sequence, protein structure, and small molecule drug, an input embedding used for input data of each respective modality is distinct from an input embedding used for input data of any of the other modalities.

18. An apparatus, comprising a processor and an associated memory; wherein the memory stores instructions that when executed by the processor, are configured to cause the processor to:

a) receive a dataset consisting of a plurality of representations of features of a plurality of proteins:

i) wherein respective modalities of the representations include:

(1) natural language representation modality, (2) sequence representation modality, (3) structure representation modality, and (4) small molecule drug representation modality; and ii) wherein the represented features include one or more of sequence, structure, function, interactions, interactors, binding partners, attributes, and properties;

b) use the dataset to train a neural network:

i) wherein the neural network is configured to accept as input data, a query consisting of one or more of the respective modalities, and to yield as output data, a response to the query, wherein the response comprises of one or more of the respective modalities, ii) wherein the neural network has a single heads, and iii) wherein final output is a probability distribution over possible values of each modality including over auxiliary tokens;

c) use the trained neural network to generate a representation of an output ligand, in response to a query specifying conditions on the ligand; and d) synthesize the ligand.

19. The apparatus of claim 18, wherein the neural network is an autoregressive transformer.

20. The apparatus of claim 19, wherein the input query requests a peptide ligand of a specified target receptor; and wherein the synthesized ligand is a ligand of the specified target receptor.

* * * * *